US00PP17659P2

(12) United States Plant Patent
Saul

(10) Patent No.: US PP17,659 P2
(45) Date of Patent: Apr. 24, 2007

(54) ***ECHINACEA* PLANT NAMED 'EVAN SAUL'**

(50) Latin Name: *Echinacea hybrida*
Varietal Denomination: Evan Saul

(75) Inventor: Richard Saul, Cleveland, GA (US)

(73) Assignee: Itsaul Plants, Atlanta, GA (US)

( * ) Notice: Subject to any disclaimer, the term of this patent is extended or adjusted under 35 U.S.C. 154(b) by 0 days.

(21) Appl. No.: 11/293,777

(22) Filed: Dec. 2, 2005

(51) Int. Cl.
*A01H 5/00* (2006.01)

(52) U.S. Cl. ..... Plt./263

(58) Field of Classification Search ..... Plt./263
See application file for complete search history.

*Primary Examiner*—Kent Bell
*Assistant Examiner*—Annette H Para
(74) *Attorney, Agent, or Firm*—C. A. Whealy

(57) ABSTRACT

A new and distinct cultivar of *Echinacea* plant named 'Evan Saul', characterized by its upright and columnar plant habit; vigorous and freely branching growth habit; inflorescences with orange-colored ray florets and dark purple-colored receptacle spines; and good garden performance.

1 Drawing Sheet

Botanical designation: *Echinacea hybrida.*
Cultivar denomination: 'Evan Saul'.

BACKGROUND OF THE INVENTION

The present Invention relates to a new and distinct cultivar of *Echinacea* plant, botanically known as *Echinacea hybrida,* and hereinafter referred to by the name 'Evan Saul'.

The new *Echinacea* is a product of a planned breeding program conducted by the Inventor in Dahlonega, Ga. The objective of the breeding program is to develop new *Echinacea* cultivars with large inflorescences with and unique ray floret coloration.

The new *Echinacea* originated from a cross-pollination made by the Inventor in August, 2002 of two unnamed *Echinacea hybrida* selections, not patented. The new *Echinacea* was discovered and selected as a single flowering plant by the Inventor in a controlled environment in Dahlonega, Ga. in June, 2003 from the resultant progeny of the stated cross-pollination. The new *Echinacea* was selected on the basis of its unique ray floret coloration.

Asexual reproduction of the new *Echinacea* by tissue culture was first conducted in Chamblee, Ga. in August, 2003. Since then, asexual reproduction by tissue culture has shown that the unique features of this new *Echinacea* are stable and reproduced true to type in successive generations.

SUMMARY OF THE INVENTION

The cultivar Evan Saul has not been observed under all possible environmental conditions. The phenotype may vary somewhat with variations in environment such as temperature and light intensity without, however, any variance in genotype.

The following traits have been repeatedly observed and are determined to be the unique characteristics of 'Evan Saul'. These characteristics in combination distinguish 'Evan Saul' as a new and distinct *Echinacea:*

1. Upright and columnar plant habit.
2. Vigorous and freely branching growth habit.

3. Inflorescences with orange-colored ray florets and dark purple-colored receptacle spines.
4. Good garden performance.

Plants of the new *Echinacea* differ primarily from plants of the parental selections in ray floret coloration.

Plants of the new *Echinacea* can be compared to plants of the *Echinacea* cultivar Sunset, disclosed in U.S. Plant Pat. No. 16,424. In side-by-side comparisons conducted in Dahlonega, Ga., plants of the new *Echinacea* differed from plants of the cultivar Sunset in the following characteristics:

1. Leaves of plants of the new *Echinacea* were larger and smoother than leaves of plants of the cultivar Sunset.
2. Plants of the new *Echinacea* had smaller discs than plants of the cultivar Sunset.
3. Plants of the new *Echinacea* and the cultivar Sunset differed in ray floret coloration as plants of the cultivar Sunset had darker orange-colored ray florets.
4. Ray florets of plants of the new *Echinacea* were not as recurved as ray florets of plants of the cultivar Sunset.

BRIEF DESCRIPTION OF THE PHOTOGRAPH

The accompanying colored photograph illustrates the overall appearance of the new *Echinacea* showing the colors as true as it is reasonably possible to obtain in colored reproductions of this type. Colors in the photograph may differ from the color values cited in the detailed botanical description which accurately describe the colors of the new *Echinacea.* The photograph comprises a side perspective view of a typical flowering plant of 'Evan Saul'.

DETAILED BOTANICAL DESCRIPTION

The aforementioned photographs and following observations and measurements describe plants grown in Dahlonega, Ga., in an outdoor nursery under full sun conditions during the summer. When the plants were about eight months old, the photographs, observations and measurements were taken. Plants used for the detailed description were grown in one-gallon containers. At that time, day temperatures averaged 29° C. and night temperatures averaged 21° C. Color references are made to The Royal Horticultural Society Colour Chart, 1995 Edition, except where general terms of ordinary dictionary significance are used.

Botanical classification: *Echinacea hybrida* cultivar Evan Saul.

Parentage:

*Female, or seed, parent.*—Unnamed *Echinacea hybrida* selection, not patented.

*Male, or pollen, parent.*—Unnamed *Echinacea hybrida* selection, not patented.

Propagation:

*Type.*—By tissue culture.

*Time to initiate roots.*—About 14 days at 24° C.

*Time to produce a rooted young plant, summer.*—About 45 days at 29° C.

*Time to produce a rooted young plant, winter.*—About 56 days at 21° C.

*Root description.*—Thick, fleshy and freely branching; white, close to 155A, in color.

Plant description:

*Appearance.*—Perennial herbaceous container and garden plant. Upright and columnar plant habit; narrow inverted triangle. Freely basally branching; about nine basal branches per plant. Vigorous growth habit.

*Plant height.*—About 31.5 cm.

*Plant width or area of spread.*—About 37 cm.

*Basal branches.*—Length: About 28 cm. Diameter: About 6 mm. Internode length: About 3.75 cm. Aspect: Upright. Strength: Strong. Texture: Pubescent. Color: 144A.

*Foliage description.*—Arrangement: Basal leaves, opposite; after flowering, alternate; simple. Length: About 12.75 cm. Width: About 4.2 cm. Shape: Lanceolate; elongated. Apex: Acuminate. Base: Attenuate. Margin: Entire. Venation pattern: Parallel. Texture, upper and lower surfaces: Pubescent; rough. Color: Developing and fully expanded foliage, upper surface: Darker green than 147A. Developing and fully expanded foliage, lower surface: Close to 147B. Venation, upper surface: Close to 146A. Venation, lower surface: Close to 145C. Petiole: Length: About 12.5 cm. Diameter: About 6 mm. Texture, upper and lower surfaces: Pubescent. Color, upper and lower surfaces: Close to 144A to 144B.

Inflorescence description:

*Appearance.*—Terminal inflorescences held above the foliage on strong peduncles. Composite inflorescence form, radially symmetrical; elongate oblong-shaped ray florets; disc florets massed at the center; ray and disc florets develop acropetally on the receptacle. Inflorescences persistent. Inflorescences face upright.

*Time of flowering.*—Long flowering period; plants flower freely from the late spring and continue to flower continuously until the autumn in Dahlonega, Ga.

*Postproduction longevity.*—Inflorescences maintain good color and substance for about two weeks on the plant.

*Quantity of inflorescences.*—One inflorescence per stem; about six open inflorescences and flower buds per plant.

*Fragrance.*—Sweet; honey or rose-like.

*Inflorescence bud.*—Length: About 1.1 cm. Diameter: About 9 mm. Shape: Ovoid; conical. Color: More green than 147A.

*Inflorescence size.*—Diameter: About 7.75 cm. Depth (height): About 2.4 cm. Disc diameter: About 3.4 cm. Receptacle diameter: About 9 mm. Receptacle height: About 8 mm. Receptacle shape: Conical.

*Ray florets.*—Length: About 3.8 cm. Width: About 1 cm. Shape: Elongated oblong. Apex: Acute or emarginate. Base: Attenuate. Margin: Entire. Texture, upper and lower surfaces: Smooth, glabrous; satiny; longitudinally ridged. Orientation: Initially upright and eventually slightly arching. Number of ray florets per inflorescence: About 20 in a single whorl. Color: When opening, upper surface: Close to 34B. When opening, lower surface: Close to 34B to 34C. Fully opened, upper surface: Close to 34B to 34C. Fully opened, lower surface: Close to 34C.

*Disc florets.*—Shape: Elongated tubular. Apex: Five-pointed; acute. Length: About 6 mm. Width: About 2 mm. Number of disc florets per inflorescence: Numerous; massed at the center of the inflorescence. Color: Immature: Close to 144A. Mature, apex and mid-section: Close to 144A to 144B. Mature, base: Close to 155D.

*Receptacle scales.*—Arrangement: One per disc floret; conspicuous, larger than disc florets. Length: About 3 cm. Diameter: About 1.5 mm. Shape: Elongate; spinescent; sharply acuminate. Texture: Stiff; smooth. Color: Apex: Close to 34A tipped with 183A to 185A. Mid-section: Close to 144A. Base: Close to 155D.

*Phyllaries.*—Quantity per inflorescence: Numerous in about four whorls. Length: About 1.3 cm. Diameter: About 4 mm. Shape: Lanceolate. Apex: Acuminate. Base: Fused to receptacle. Margin: Entire. Texture, upper and lower surfaces: Pubescent. Color, upper and lower surfaces: More green than 147A.

*Reproductive organs.*—Androecium: Present on disc florets only. Stamen number: About five per floret. Anther shape: Elongated oblong. Anther length: About 2 mm. Anther color: Close to 202A. Pollen amount: Moderate. Pollen color: Close to 15A. Gynoecium: Present on both ray and disc florets. Pistil number: One per floret. Pistil length: About 4 mm. Stigma shape: Two-parted. Stigma color: Close to 6A.

*Seed/fruit.*—Seed and fruit development has not been observed.

Disease/pest resistance: Resistance to pathogens and pests common to *Echinaceas* has not been observed on plants grown under outdoor conditions.

Garden performance: Plants of the new *Echinacea* have been observed to have good garden performance and to tolerate wind and rain. Plants of the new *Echinacea* have been observed to tolerate temperatures from −15° C. to 35° C.

It is claimed:

1. A new and distinct cultivar of *Echinacea* plant named 'Evan Saul', as illustrated and described.

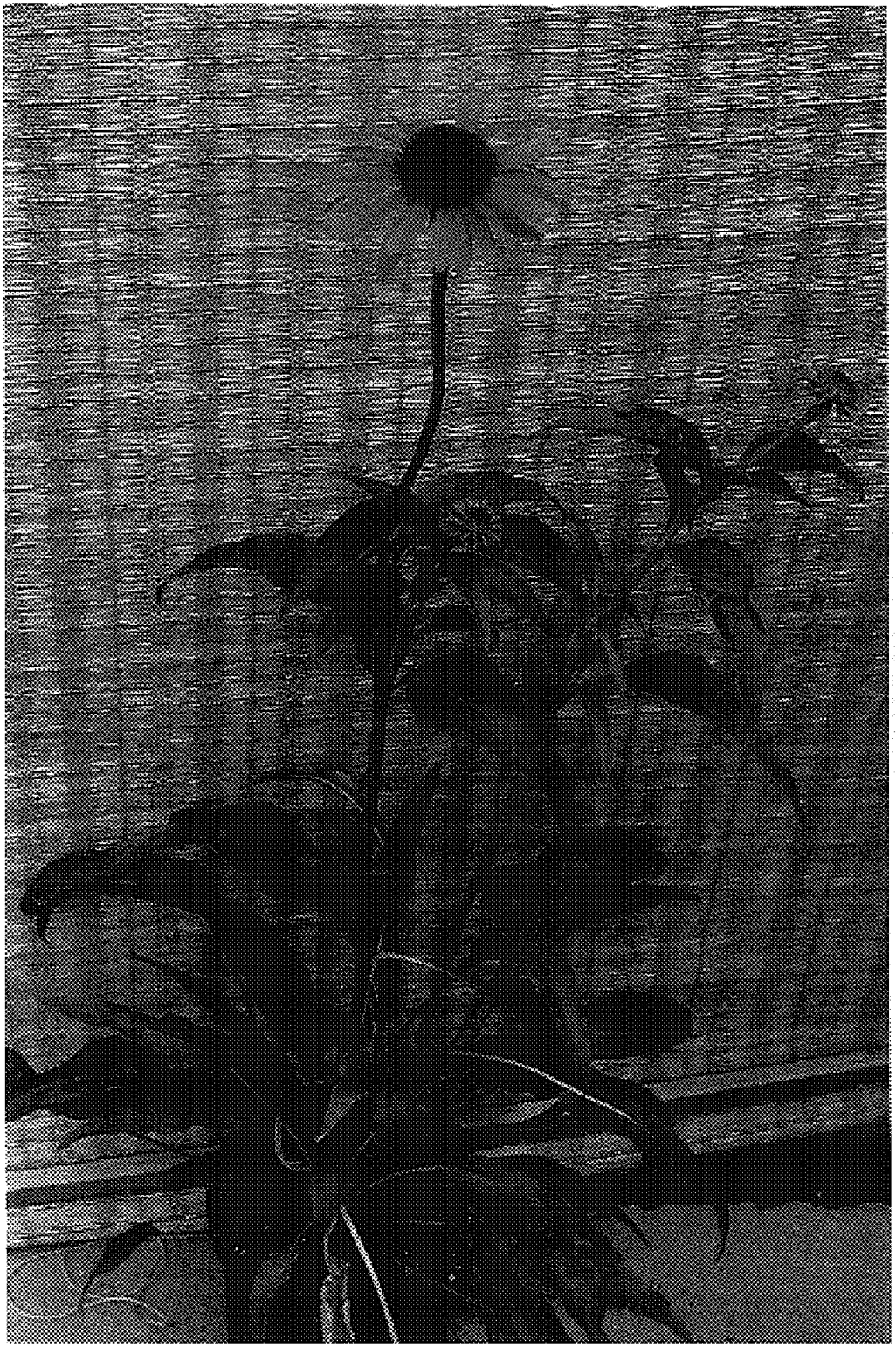

* * * * *